United States Patent [19]

McRae

[11] Patent Number: Plant 6,523

[45] Date of Patent: Jan. 10, 1989

[54] LILY NAMED COPELLIA

[75] Inventor: Edward A. McRae, Boring, Oreg.

[73] Assignee: Melridge, Inc., Aurora, Oreg.

[21] Appl. No.: 23,780

[22] Filed: Mar. 9, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinct variety of hybrid lily bearing large, upright to semi-upright flowers of excellent form particularly characterized by their clear pink coloration extending along the midrib of each tepal and suffuxing laterally toward a pure white petal margin which meets from each side to form a pure white outer end and tip of each tepal. This combination of large size and coloration and the upright to semi-upright orientation of the flowers of this plant is completely new in the Oriental hybrid divisions of lilies suited to forcing and to mass commercial cultivation. The plant is highly resistant to disease and shows tolerance of virus; it is an excellent garden plant; and the bulbs may be precooled and forced for cut flower production.

1 Drawing Sheet

BACKGROUND OF THE NEW PLANT

This new lily plant variety originated as a seedling which first flowered at Sandy, Ore., in 1970, the mother plant for this seedling being a selected clone from the strain 'Pink Glory' (unpatented) which I crossed with a selected form of the species *Lilium nobilissum* (unpatented) as the pollen parent, the crossing of these distinctly unrelated varieties being done under extremely high greenhouse temperatures maintained for at least one week after pollination. The objective of this crossing was the production of a large flowered, generally upright Oriental lily hybrid in shades of soft pink and white suited for forcing into flower out-of-season, heretofore unknown in the lily breeding art. The selection of this particular seedling for propagation was done because it had an upright to semi-upright orientation of its flowers, which were of extremely large size and broad tepalled in a bowl-shaped form; and because the flowers had a distinctive clear pink coloration bordered with a white margin of medium width, unique among Oriental hybrid lilies, and because the plant possessed an unusually strong, stout stem with exceptionally broad leaves. Reproduction of this selected seedling was done by me at Sandy, Ore., by bulb scale propagation and it was found that the clone possesses to a high degree the desirable characteristics of hybrid vigor, great hardiness, and disease resistance. The clone was also found to be a vigorous and good grower and propagator as observed under testing at Sandy, Ore.

Successive generations of this new plant produced by natural propagation from bulblets, by bulb scale propagation, and by tissue culturing from bulb scale explants have demonstrated that the novel and distinctive characteristics of this new variety of lily are fixed and hold true under asexual propagation from generation to generation and appear to be firmly fixed.

Work with this new variety has also demonstrated that it is well suited for forcing out-of-season when the bulbs are dug at the appropriate time and properly precooled. For example, late October-dug bulbs, properly precooled and potted in January, will flower under glass in western Oregon in an average of one hundred ten to one hundred fifteen days, with no supplementary lighting and at moderate greenhouse temperatures.

DESCRIPTION OF THE DRAWING

My new variety of lily plant is illustrated by the accompanying photographic drawing which shows the open bloom in full color and shows the flower form, the tepal arrangement, and its clear pink coloration with a moderately wide white margin; the colors shown being as nearly true to those herein specified as is possible to obtain by conventional, professional photographic procedures.

DESCRIPTION OF THE NEW VARIETY

The following is a detailed description of my new variety of Asiatic hybrid lily, with nomenclature according to The International Lily Register, 2nd edition, 1969, by The Royal Horticultural Society of London, England, and with color designations according to the R.H.S. Colour Chart published by the society in 1966.

THE PLANT

Origin: Seedling.

Parentage:

*Seed parent.*—A selected clone from the 'Pink Glory' strain (unnamed and unpatented).

*Pollen parent.*—A selected clone of *Lilium nobilissum* (unpatented).

Classification:

*Botanic.*—Division VII-B, bowl-shaped Oriental hybrid lily, according to The Horticultural Classification of Lilies by The Royal Horticultural Society of London, England.

*Commercial.*—Hybrid Lilium Clone.

Form: A single stem, erect and stately.

Height: About 70 to 150 cm. from bulbs of about 14 to 18 cm. in circumference, provided that their light levels are adequate; low light levels may cause "stretching".

Growth: Vigorous and upright.

Foliage:

*Quantity.*—Abundant.

*Size of leaf.*—About 12 to 15 cm. long and unusually broad with a width of about 7 to 8 cm.

*Shape of leaf.*—Elliptical with acuminate tip.

*Texture.*—Leathery.

*Aspect.*—Glossy.

*Color.*—Medium green, lighter on the lower side.

The bulb:

*Size.*—The bulb may be of any size, ranging to about 25 cm. in circumference in commercial use.

*Color.*—White, with flushes of soft pink or soft yellow after exposure to light.

THE BUD

Form: Long ovoid with rounded base and obtuse tip.

Size: About 9 to 12 cm. long and about 10 to 12 cm. in circumference just prior to opening.

Opening rate: The bud opens slowly, taking about one hour in response to morning light.

Color: White, with a shoft flush of pink in the middle of the bud and with soft green midribs.

Peduncle:

*Length.*—Averages about 4 to 6 cm., but may become elongated if light levels are too low or if the bulbs have been improperly stored prior to forcing.

*Color.*—Medium green with a very light plum overlay.

THE FLOWER

Blooming habit: Once annually and profusely in midseason.

Size: Very large, averaging about 18 to 23 cm. in diameter, reflexing at the tips on the second day to leave a top side spread of about 15 to 18 cm.

Borne: As a single raceme having three to six flowers from a bulb about 14 to 16 cm. in circumference.

Shape: A broad bowl shape by the second day, with the "bowl" about 10 cm. deep.

Tepalage: Typical of genus Lilium with six imbricated tepals generally ovate with acuminate tip.

Size:

*Length.*—About 9 to 12 cm.

*Width.*—Outer tepals — About 3 to 3.5 cm. Inner tepals — About 5 to 5.5 cm.

Color: The flowers are distinguished by the clear pink, 66C-D, of a central stripe, extending from the base of the tepal toward the tip, which suffuses laterally from along the midrib just above the nectaries to lighter pinks, from 68A through B-C, near the tepal margins which are pure white from 1 to 2 cm. wide along each of the tepal margins toward the outer end portion of the tepal where the margins join to become solid white to within about 3 cm. from the tepal apex.

*Spotting.*—These flowers have only a few small and inconspicuous pink spots, five to twenty of medium size being found on each inner tepal parallel with the nectary.

*Aspect.*—Shiny.

*Persistence.*—The tepals stay on the stems about three weeks.

Pedicel:

*Length.*—About 8 to 12 cm., in average.

*Character.*—Sturdy and ascending up to about 45 degrees from the horizontal.

*Color.*—Medium green with light plum overlay.

Color changes: The flowers become slightly lighter and a more lavender-toned pink, approaching 65D-C to 68D, as the flower ages. Low light levels and extreme heat may cause the pink pigmentation to decrease.

Disease resistance: Both flower and plant are resistant to disease; and in particular, they are resistant to Fusarium bulb rot and Botrytis blight.

Fragrance: Distinctive and pleasing.

Lasting qualtity: The flower is long lasting, both on the plant and as a cut flower.

REPRODUCTIVE ORGANS

Stamens:

*Number.*—Six, with arrangement typical of genus Lilium.

*Anthers (dehisced) and pollen.*—Grayed red, 179A, in color.

*Filaments.*—Length: About 8 to 10 cm. Color: Soft green to white.

Pistil:

*Number.*—One.

*Style.*—About 8 to 10 cm. long.

*Stigma.*—Size: Large. Color: Soft greenish white to very light pink.

Character of ovary: The ovary is characteristic of the genus Lilium.

THE FRUIT

Fertility: The fruit is fertile.

Shape: Ovoid.

Color at maturity: Soft brown, sometimes overlaid with soft plum.

This new variety of Oriental hybrid lily most nearly resembles that variety 'Pink Glory' (unpatented) but it has much larger and thicker and more bowl-shaped flowers which are upright to semi-upright rather than side-facing in orientation. Its leaves are much broader and its stems are stronger and stockier than those of 'Pink Glory'.

I claim:

1. The new and distinctive variety of Oriental hybrid lily plant and the parts thereof, substantially as herein shown and described, and particularly characterized by its unique upright to semi-upright flowers which have a clear pink coloration along the midrib of each tepal and between moderately broad, white tepal margins; and by its vigorous growth; the excellence of its flower form and substance; and its versatility both as a garden plant and as a cut flower producer from precooled bulbs forced under glass out-of-season.

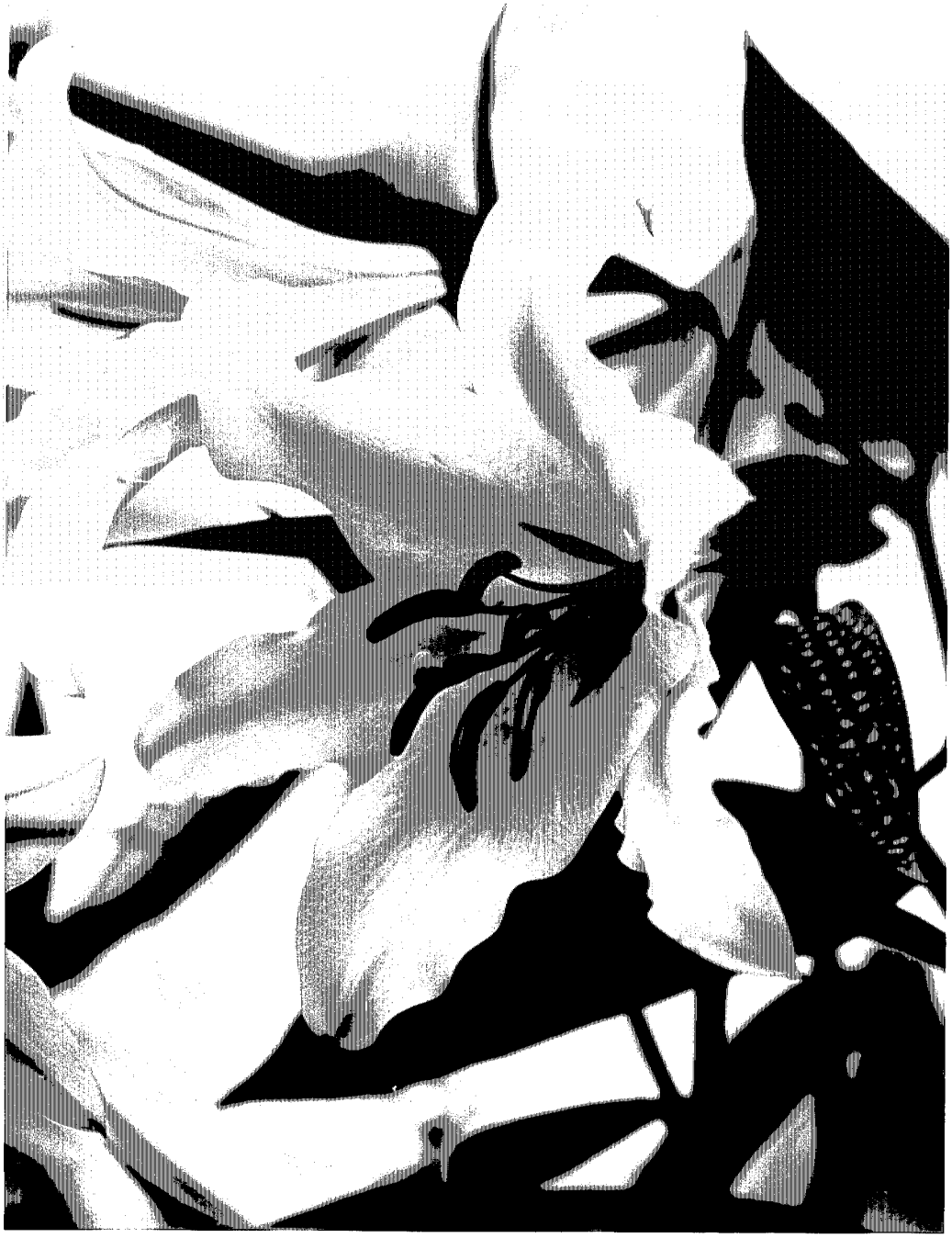

* * * * *